United States Patent [19]

Sjoerdsma et al.

[11] 4,399,151

[45] Aug. 16, 1983

[54] METHOD OF INHIBITING THE GROWTH OF PROTOZOA

[75] Inventors: Albert Sjoerdsma; Peter P. McCann, both of Cincinnati, Ohio

[73] Assignee: Merrell Dow Pharmaceuticals Inc., Cincinnati, Ohio

[21] Appl. No.: 262,275

[22] Filed: May 11, 1981

Related U.S. Application Data

[63] Continuation-in-part of Ser. No. 159,973, Jun. 16, 1980, abandoned.

[51] Int. Cl.³ ............... A61K 31/195; A61K 31/13; A61K 31/70
[52] U.S. Cl. .................................. 424/319; 424/180; 424/325
[58] Field of Search .................. 424/180, 319, 325

[56] References Cited

U.S. PATENT DOCUMENTS 4,267,374  5/1981  Metcalf et al. .................... 424/325

FOREIGN PATENT DOCUMENTS 868882  11/1978  Belgium .

OTHER PUBLICATIONS

Cohen, Science, vol. 205, 964–71 (1979).
Abdel-Monem et al., J. Med. Chem., vol. 17, No. 4, 447–451 (1974).

Primary Examiner—John M. Ford
Attorney, Agent, or Firm—William J. Stein; Raymond A. McDonald; Gary D. Street

[57] ABSTRACT

α-Substituted amines and α-substituted-α-amino acids are described which are useful in inhibiting the growth of protozoa in animals.

16 Claims, No Drawings

METHOD OF INHIBITING THE GROWTH OF PROTOZOA

DESCRIPTION

This application is a continuation-in-part application of U.S. Ser. No. 159,973, filed June 16, 1980, now abandoned.

TECHNICAL FIELD

This invention relates to certain α-substituted amines and α-substituted-amino acids which are useful in inhibiting the growth of protozoe in animals and particularly in poultry.

BACKGROUND ART

Polyamines have been implicated in many aspects of cell division. Impairment of the biosynthesis of polyamines by means of enzyme inhibitors is believed to cause a decrease in cell proliferation in mammals. Although the physiological role of polyamines has not been clearly delineated, there is evidence to suggest their involvement with cell division and growth, H. G. Williams-Ashman et al., The Italian J. Biochem. 25, 5–32 (1976), A. Raina and J. Janne, Med. Biol. 53, 121–147 (1975) and D. H. Russell, Life Sciences 13, 1635–1647 (1973).

Polyamines are also known to be essential growth factors for certain microorganisms, as for example *E. coli*, Enterobacter, Klebsiella, *Staphylococcus aureus*, *C. cadaveris*, *Salmonella typhosa* and *Haemophilus parainfluenza*. There is evidence to suggest that polyamines are associated with both normal and neoplastic mammalian cell growth, there being an increase in both the synthesis and accumulation of polyamines following a stimulus causing cellular proliferation. It is also known that there is a correlation between polyamine formation and the activity of the decarboxylase enzymes of ornithine, S-adenosylmethionine, arginine and lysine. The term polyamine is taken to include the diamine putrescine and the polyamines spermidine and spermine. Putrescine is the decarboxylation product of ornithine, catalyzed by ornithine decarboxylase. Putrescine formation may also occur by decarboxylation of arginine to form agmatine, which is hydrolyzed to give putrescine and urea. Arginine is also involved in ornithine formation by action of the enzyme arginase. Activation of methionine by the enzyme S-adenosylmethionine synthetase forms S-adenosylmethionine which is decarboxylated. The propylamine moiety of the activated methionine may then be transferred to putrescine to form spermidine. Alternatively, the propylamine moiety may be transferred to spermidine to form spermine. Hence, putrescine serves as a precursor to spermidine and spermine. Additionally, putrescine has been shown to have a marked regulatory effect upon the polyamine biosynthetic pathway. Also an increased synthesis of putrescine has been shown to be an early indication that a tissue will undergo renewed growth processes. Cadaverine, which is the decarboxylation product of lysine, has been shown to stimulate the activity of S-adenosylmethionine decarboxylase and is known to be essential to the growth processes of many microorganisms, for example, *H. parainfluenza*.

The rationale of polyamine metabolism has been suggested by Cohen, Science 205, 964 (1979). The apparent unique role of polyamine metabolism in trysanosomes and the dependence of trysanosomes upon ornithine decarboxylase as a source of putrescine further supports our observations that certain specific ornithine decarboxylase inhibitors of polyamine synthesis are highly effective in inhibiting the growth of protozoa.

SUMMARY OF THE INVENTION

We have discovered that certain compounds that belong to a class of irreversible inhibitors of ornithine decarboxylase are useful in inhibiting the growth of protozoa. Moreover, this inhibition occurs throughout a wide spectrum of protozoa such as with members of the subphylum Sarcomastigophora and Sporozoa. More particularly, the class of compounds hereinafter described are particularly useful in inhibiting the growth of members of the superclass of Mastigophora, specifically *Trypanosoma brucei brucei* and members of the class of Telosporea, specifically *Eimeria tenella* the organism which causes cocidiosis in poultry.

The compounds useful in the practice of this invention are α-substituted amines or α-substituted-α-amino acids having the general formula

wherein R₁ is hydrogen or carboxy; Y is selected from the group consisting of CH₂F, CHF₂, CF₃ and C≡CH; Z is selected from the group consisting of H₂N—(CH₂)₃,

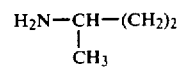

and H₂N—CH₂CH=CH; with the proviso that when R₁ is hydrogen, Y cannot be CF₃ and Z must be

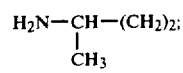

and the salts and individual optical isomers thereof.

When administered in vivo to animals containing active protozoal infections, the compounds of formula (I) can be utilized to treat such animals by inhibiting the further growth of the protozoal infections. Alternatively, the compounds described above can be administered prophylactically to prevent such protozoal infections from occurring.

DETAILED DESCRIPTION OF THE INVENTION

In general formula (I) above the symbol R₁ is represented either by hydrogen or a carboxyl group. Where the symbol R₁ is hydrogen a class of α-substituted amines is delineated. Where the symbol R₁ is the carboxyl group, a class of α-substituted-α-amino acids is delineated.

The symbol Y represents either an acetylenic group or a fluoro-substituted methyl group. The fluoro-substituted methyl groups are illustrated by the monofluoromethyl, difluoromethyl or trifluoromethyl radicals.

The symbol Z represents either the 3-aminopropyl group, the 3-amino-3-methylpropyl group or the 3- amino-1-propylene group. The saturated groups, viz. the 3-aminopropyl group and the 3-amino-3-methylpropyl group represent the preferred side chains.

The proviso limitation is intended to exclude certain classes of diamines from the scope of compounds encompassing this invention. Excluded from the invention via this proviso limitation are α-substituted diamines wherein the symbol Z is the 3-aminopropyl group or the 3-amino-1-propylene group, i.e., those compounds having the general formulae

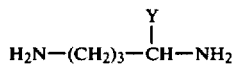  (II)

and

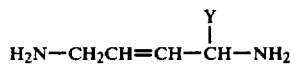  (III)

wherein the symbol Y is as previously defined.

Specifically excluded from the remaining α-substituted diamines is the species wherein the symbol Y represents the trifluoromethyl group. Thus, compound (IV), 4-methyl-1-trifluoromethyl-1,4-butanediamine, is specifically excluded from the scope of compounds which can be usefully employed.

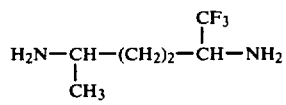  (IV)

Included within the scope of compounds that can be employed are α-substituted amino acids having the formula:

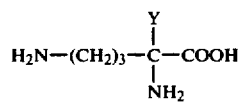  (V)

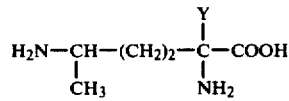  (VI)

and

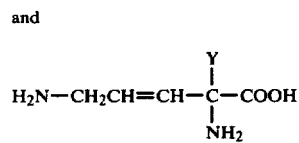  (VII)

In formulae (V), (VI) and (VII) above, the symbol Y is as previously defined.

The α-substituted amines included within the scope of compounds that can be usefully employed in the practice of this invention are defined by the general formula

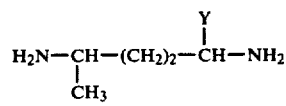  (VIII)

wherein the symbol Y represents the CH₂F, CHF₂ and C≡CH groups, but in the case of the diamines exludes the CF₃ group.

Illustrative examples of the salts of the compounds of this invention include non-toxic acid addition salts formed with inorganic acids, such as, hydrochloric, hydrobromic, sulfuric and phosphoric acid, and organic acids, such as, methanesulfonic, salicyclic, maleic, malonic, tartaric, citric, cyclamic and ascorbic acids.

A preferred class of compounds of this invention are those compounds in which the symbol Y represents the difluoromethyl group. Another preferred class of compounds sis delineated where the symbol Z represents the 3-aminopropyl moiety or the 3-amino-3-methylpropyl moiety.

In addition to the salts indicated above, the term salts is taken to include those internal salts or zwitter-ions of those compounds of formula (I) above that are amphoteric in nature. Moreover, whereas the optical configuration for the compounds described herein is not specifically designated, it is recognized that the α-carbon atom possesses an asymmetric center and that individual optical isomers of these compounds exist. Accordingly, both the d- and l-optical isomers as well as the racemic mixtures are contemplated as being within the scope of this invention.

Lactam formation can occur where the symbol $R_1$ represents the carboxyl group and the symbol Z represents the 3-aminopropyl moiety or the 3-amino-3-methylpropyl moiety as represented by the following general formula

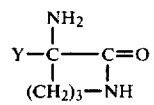  (IX)

In the above general formula the symbol Y is an originally described. Where the symbol Z represents the 3-amino-3-methylpropyl moiety, the (CH₂)₃ group in formula (IX) above can be additionally substituted with a 3-methyl group.

Illustrative examples of compounds useful in accordance with the teachings of this invention include:
2,5-diamino-2-(fluoromethyl)pentanoic acid,
2,5-diamino-2-(difluoromethyl)pentanoic acid,
2,5-diamino-2-(trifluoromethyl)pentanoic acid,
2,5-diamino-2-(ethynyl)pentanoic acid,
2,5-diamino-2-fluoromethyl-5-methylpentanoic acid,
2,5-diamino-2-difluoromethyl-5-methylpentanoic acid,
2,5-diamino-2-trifluoromethyl-5-methylpentanoic acid,
2,5-diamino-2-ethynyl-5-methylpentanoic acid,
2,5-diamino-2-fluoromethyl-3-pentenoic acid,
2,5-diamino-2-difluoromethyl-3-pentenoic acid,
2,5-diamino-2-trifluoromethyl-3-pentenoic acid,
2,5-diamino-2-ethynyl-3-pentenoic acid,
1-fluoromethyl-4-methyl-1,4-butanediamine,
2-difluoromethyl-4-methyl-1,4-butanediamine, and
1-ethynyl-4-methyl-1,4-butanediamine.

The compounds of general formula (I) wherein Z is H₂N—(CH₂)₃; Y is CH₂F, CHF₂ and CF₃, and $R_1$ is carboxy are prepared by treating respectively an ester derivative of ornithine, wherein the amino groups are suitably protected, with a strong base to form the carbanion intermediate. This is reacted with a suitable halomethyl-halo alkylating reagent in an aprotic solvent, such as dimethylsulfoxide, dimethylformamide, dimethylacetamide, benzene, toluene, ethers, such as, tetrahydrofuran, diethyl ether or dioxane, and in the presence of a hexamethylphosphortriamide when Y is other than $F_2CH$—, at a temperature of about $-120°$ C. to $120°$ C., preferably about $25°$ to $50°$ C., for about ½ hour to 48 hours followed by acid or base hydrolysis. This can be represented by the following reaction sequence.

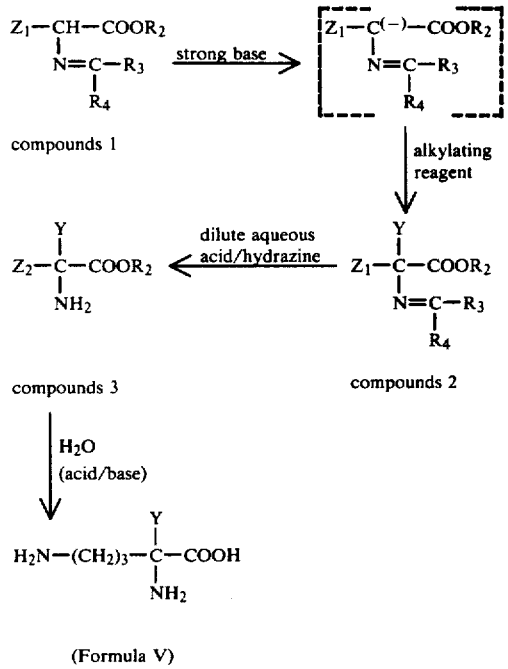

compounds 1 compounds 2 compounds 3

(Formula V)

In the above reaction sequence Y is $FCH_2$—, $F_2CH$—, $F_3C$—; $R_2$ is a lower alkyl group, for example, methyl, ethyl, isopropyl, n-propyl or n-butyl; $R_3$ is hydrogen, phenyl, a straight or branched alkyl group having from 1 to 8 carbon atoms, methoxy or ethoxy; $R_4$ is phenyl or a straight or branched alkyl group of from 1 to 8 carbon atoms; or $R_3$ and $R_4$ taken together may form an alkylene group of from 5 to 7 carbon atoms, that is, —$CH_2$—$(CH_2)_m$—$CH_2$— wherein m is an integer of from 3 to 5. Illustrative examples of straight or branched alkyl groups of from 1 to 8 carbon atoms which $R_3$ and $R_4$ may represent are, for example, methyl, ethyl, n-propyl, isopropyl, n-butyl, tert-butyl, n-pentyl, neopentyl or triethylmethyl groups. The symbol $Z_1$ is

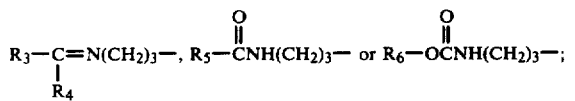

$R_3$ and $R_4$ are the same and have the meanings defined above; and each of $R_5$ and $R_6$ is phenyl, benzyl or a lower alkyl group of from 1 to 4 carbon atoms that is straight or branched, for example, methyl, ethyl or isopropyl; $Z_2$ is $H_2N(CH_2)_3$—,

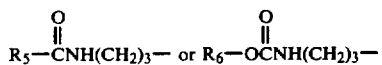

wherein $R_5$ and $R_6$ have the above defined meanings.

Suitable strong bases which may be employed in the above reaction sequence to form the carbanion intermediate are those which will abstract a proton from the carbon atom alpha to the carboxy group, such as, alkyl lithium, for example, butyl lithium or phenyl lithium, lithium di-alkylamide, for example, lithium diisopropylamide, lithium amide, tertiary potassium butylate, sodium amide, metal hydrides, for example, sodium hydride or potassium hydride, tertiary amines, such as, triethylamine, lithium acetylide or dilithium acetylide. Lithium acetylide, dilithium acetylide, sodium hydride, and lithium diisopropylamide are particularly preferred bases.

Suitable alkylating reagents which may be employed in the above reaction sequence are illustratively chlorofluoromethane, bromofluoromethane, fluoroiodomethane, chlorodifluoromethane, bromodifluoromethane, difluoroiodomethane, bromotrifluoromethane, chlorotrifluoromethane, trifluoroiodomethane, bromochloromethane, dichloromethane, chloroiodomethane, bromodichloromethane and dichloroiodomethane. These alkylating reagents are well known to the art.

Removal of the protecting groups of the amine and carboxylic acid function may be achieved in one step by treatment of compound 2 with aqueous acid, for example, hydrochloric acid or toluenesulfonic acid, at a temperature of about 0° to 100° C. for about 4 to 24 hours to give compounds of general Formula V. It is preferred to remove first the protecting groups of the amine function(s) of compounds 2 when said functions are protected as a Schiff's base by treating compounds 2 with dilute aqueous acid, for example, hydrochloric acid or with hydrazine or phenylhydrazine in solvents, such as, lower alcohols, for example, methanol or ethanol, ethers, chlorinated hydrocarbons, benzene and water. Removal of the protecting groups of the carboxylic acid function and the amine groups when the amine groups are protected other than as a Schiff's base is achieved by treatment of compounds 3 with concentrated aqueous acids, for example, hydrobromic acid at a temperature of about 0° to 100° C. or in aqueous base, for example, ammonium hydroxide.

The amine protected ester derivatives, that is, compounds 1, wherein $R_3$ is other than methoxy or ethoxy, are prepared by treating an appropriate amino acid ester with a carbonyl bearing compound to form a Schiff's base in a generally known manner, specifically: (a) when $R_3$ is hydrogen, by treating the appropriate amino acid ester with benzaldehyde or an alkanal having from 1 to 9 carbon atoms being straight or branched, for example, 1-propanal, 1-butanal, 2,2-dimethylpropan-1-al or 2,2-diethylbutan-1-al; (b) when $R_3$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone; and (c) when $R_3$ is a straight or branched alkyl group having from 1 to 8 carbon atoms, treating the appropriate amino acids ester with a phenyl alkyl ketone as described above or with a di-alkyl ketone wherein each alkyl moiety has from 1 to 8 carbon atoms and is straight or branched, for example, dimethyl ketone, diethyl ketone, methyl isopropyl ketone, di-n-butyl ketone or methyl tert-butyl ketone. The carbonyl bearing compounds are known in the art or may be prepared by procedures well known in the art.

When $R_3$ is methoxy or ethoxy in compound 1, an appropriate amino acid ester derivative is reacted with benzoyl halide or an alkanoic acid halide wherein the alkanoic acid has from 1 to 9 carbon atoms and may be straight or branched, such as, acetyl chloride, propionyl chloride, butyryl chloride, tert-butyrl chloride, 2,2-diethylbutyric acid chloride or valeryl chloride. The reaction is conducted at 0° C. in an organic solvent such as ether, methylenechloride, dimethylformamide, dimethylacetamide or chlorobenzene in the presence of an organic base such as triethylamine or pyridine. Following the reaction, the reaction mixture is allowed to warm to about 25° C. for one hour. The resulting amide derivative is combined with an alkylating reagent, such as methylfluorosulfonate, dimethylsulfate, methyliodide, methyl p-toluenesulfonate or trimethyloxonium hexafluorophosphate (when $R_3$ is methoxy) or triethyloxonium tetrafluoroborate (when $R_3$ is ethoxy) at about 25° C. in a chlorinated hydrocarbon solvent such as methylene chloride, chlorobenzene or chloroform. The reaction mixture is refluxed for about 12 to 20 hours, cooled to about 25° C. and an organic base such as triethylamine or pyridine is added after which the solution is extracted with brine and the product isolated.

When $R_3$ and $R_4$ together form an alkylene group in compounds 1 having from 5 to 7 carbon atoms, the corresponding amino acid ester derivatives are obtained by treating the amino acid ester with a cyclic alkanone to form a Schiff's base by procedures generally known in the art. Cyclic alkanones that can be employed include cyclopentanone, cyclohexanone and cycloheptanone.

When the symbol $Z_1$ in compounds 1 is

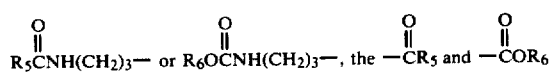

protecting groups are added to the corresponding free amino acid, i.e., ornithine, by treatment of said amino acid with an excess of a copper salt, such as copper carbonate, in boiling water for about 1 to 6 hours. Upon cooling to room temperature the insoluble materials are filtered and the filtrate is treated with an appropriate acid halide

or an appropriate alkyl or aryl haloformate

in a solvent such as acetone in the presence of a base such as sodium bicarbonate or sodium hydroxide. This treatment is followed by treatment with hydrogen sulfide. Illustrative acid halides which may be employed include acetyl chloride, propionyl chloride, benzoyl chloride or 2-phenylacetyl chloride. Illustrative haloformates which may be employed include benzyl chloroformate, phenyl chloroformate, methyl chloroformate or ethyl chloroformate.

The lactams of the compounds of general Formula I wherein $R_1$ is carboxy are prepared from the corresponding amino acid esters having the structure

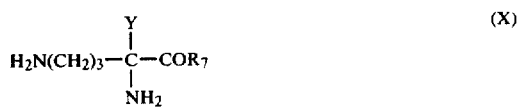

wherein Y has the meaning defined in Formula I and $R_7$ is a straight or branched alkoxy group of from 1 to 8 carbon atoms, illustratively methoxy, ethoxy, isopropoxy, butoxy or hexyloxy. The lactams are prepared by treating said amino acid esters with an appropriate base, such as sodium hydroxide, potassium hydroxide, lithium hydroxide, sodium carbonate, potassium carbonate, sodium methoxide, potassium methoxide, potassium tert-butoxide, sodium amide, or an organic amine such as a trialkylamine, for example, triethylamine in a solvent such as a lower alcohol, for example, methanol, ethanol, isopropyl alcohol, n-butanol, water, dimethylformamide, dimethylsulfoxide, hexamethylphosphortriamide or mixtures thereof. The reaction is conducted for a period of from ½ hour to 24 hours at a temperature of from about 0° to 120° C., optionally under a nitrogen atmosphere. The compounds of general Formula (X) are obtained by procedures well known to the art, for example, by utilizing the corresponding amino acid and treating said amino acid with an appropriate alcohol such as methanol, ethanol, isopropyl alcohol, n-butanol or n-heptanol saturated with HCl gas.

The compounds of general formula I wherein Z is

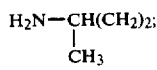

Y is $CH_2F$, $CHF_2$ and $CF_3$, and $R_1$ is carboxy are prepared via procedures that are analogous to those just described.

Compounds of general Formula I wherein Z is

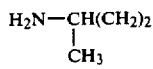

or $H_2N—(CH_2)_3$, Y is C CH and $R_1$ is carboxy are prepared by treating a suitably protected propargylamine derivative, such as a silyl derivative, with a strong base to form a protected propargylamine carbanion intermediate. This carbanion intermediate is reacted with an alkylating reagent of the formula $R_8X$, wherein X is a halogen such as chlorine or bromine, and $R_8$ is $PhHC=N(CH_2)n—$ in which n is the integer 3. The thus formed alkylated protected propargylamine derivative is then treated with a strong base to form an alkylated protected propargylamine carbonaion. The second carbanion is reacted with an acylating reagent and the protecting groups are subsequently removed by acid or base hydrolysis as indicated in the following reaction scheme:

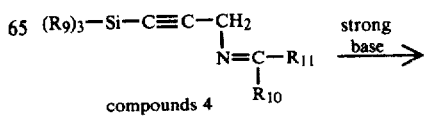

compounds 4

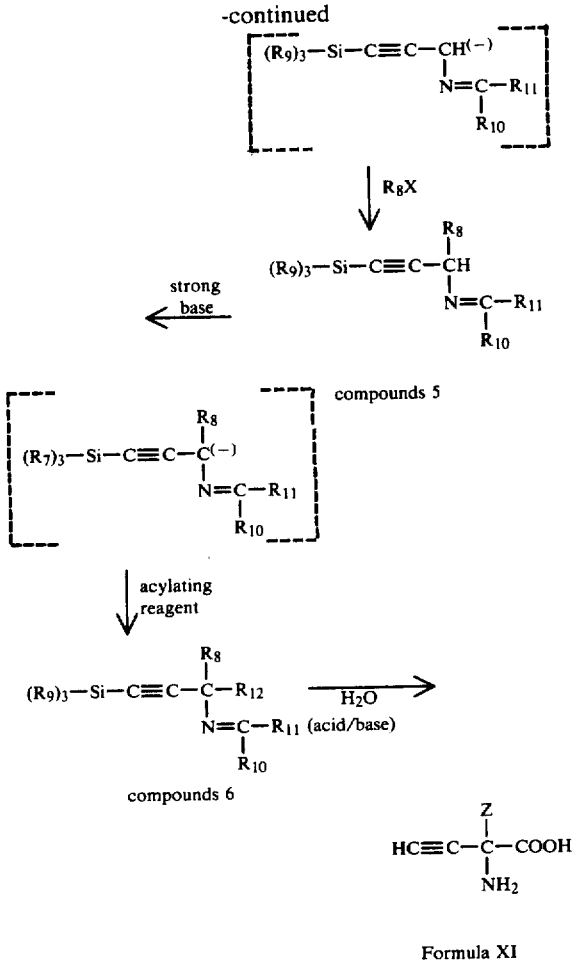

compounds 6

$$HC\equiv C-\underset{\underset{NH_2}{|}}{\overset{\overset{Z}{|}}{C}}-COOH$$

Formula XI

In the above reaction scheme $R_8$ and X have the meanings defined hereinabove, Ph represents phenyl, $R_{10}$ is hydrogen, methoxy or ethoxy, $R_{11}$ is phenyl, tert-butyl, or triethylmethyl, $R_9$ is a straight or branched lower alkyl group having from 1 to 4 carbon atoms, $R_{12}$ is a carboxy anion, a carboxylic acid ester, a carboxamide, a nitrile or other group capable of being hydrolyzed to a carboxylic acid function, and Z is

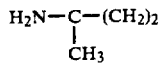

or $H_2N(CH_2)_3$.

Suitable strong bases which may be employed in the above reaction to form each carbanion are those which will abstract a proton from the carbon atom adjacent to the acetylene moiety, such as an alkyl lithium. Suitable alkylithium compounds that may be employed include butyl lithium or phenyl lithium, lithium diisopropylamide, lithium amide, tertiary potassium butylate and sodium amide.

The alkylating reagents, $R_8X$, employed in the above reaction are known to the art and can be prepared by standard procedures known in the art. Thus, the reactant $PhHC=N(CH_2)n-$ can be prepared, for example, by reacting 3-bromo-n-propylamine hydrochloride or 4-bromo-n-butylamine hydrochloride with benzaldehyde in the presence of an organic amine, such as, triethylamine in a suitable solvent. Solvents that can be employed include diethyl ether, tetrahydrofuran, dioxane, chloroform or dichloromethane.

Suitable acylating reagents which may be employed in the above reaction are halo-formates, such as chloro methylformate or chloro ethylformate, azido tert-butylformate, cyanogen bromide, carbon dioxide, diethylcarbonate, phenylisocyanate, triethoxymethlium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis by means of a lower alcohol, such as ethanol or isopropyl alcohol is required prior to hydrolysis of the protecting groups.

The alkylating reaction is readily conducted in the presence of an aprotic solvent such as benzene, toluene, ether, tetrahydrofuran, dimethylsulfoxide, dimethylformamide, dimethyl acetamide, hexamethyl phosphortriamide. The reaction temperature varies from $-120°$ C. to about $25°$ C., a preferred reaction temperature being about $-70°$ C., with the reaction period ranging from about ½ hour to 24 hours.

Removal of the protecting groups, as represented in the foregoing reaction scheme in the step relating to the conversion of compounds 6 to the compounds of Formula XI, is achieved by treatment of compounds 6 with an aqueous acid such as hydrochloric acid or toluene sulfonic acid. Alternatively, an aqueous base such as sodium hydroxide or potassium hydroxide, or hydrazine or phenylhydrazine may be employed.

The propargylamine derivatives of compounds 4 wherein $R_{10}$ is hydrogen are prepared by the addition of protecting groups on the acetylene function and the nitrogen function of propargylamine. Protection of the nitrogen function of the propargylamine is accomplished by forming a Schiff's base with a nonenolizable carbonyl bearing compound such as benzaldehyde, 2,2-dimethylpropanal or 2,2-diethylbutanal. Protection of the acetylenic function is accomplished by reacting the above-described Schiff's base with a tri-alkylsilyl chloride wherein the alkyl moiety has from 1 to 4 carbon atoms and is either straight or branched. Trialkylsilyl chlorides that can be utilized include trimethylsilylchloride or triethylsilylcloride.

The propargylamine derivatives of compounds 4, wherein $R_{10}$ is methoxy or ethoxy are prepared by reacting propargylamine wherein the acetylene function is protected by a trialkylsilyl group with benzoyl chloride, pivalic acid chloride, or 2,2-diethylbutyric acid chloride at 0° C. in a suitable solvent. Suitable solvents include diethyl ether, dioxane, tetrahydrofuran, chloroform, methylenechloride, dimethylformamide, dimethylacetamide, or chlorobenzene. The reaction is conducted in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_{10}$ is methoxy, or triethyloxonium tetrafluoroborate when $R_{10}$ is ethoxy, at about 25° C. in a chlorinated hydrocarbon solvent such as methylene chloride, chlorobenzene or chloroform. The reaction mixture is refluxed for about 12 to 20 hours, cooled to about 25° C. and an organic base such as triethylamine or pyridine is added.

The resulting solution is extracted with brine and the desired product isolated therefrom.

The protected propargylamine starting material is obtained by treating a 3-trialkylsilylprop-2-ynyl-1-iminobenzyl derivative, that is compounds 4 wherein $R_{10}$ is hydrogen and $R_{11}$ is phenyl, with hydrazine or phenylhydrazine at about 25° C. for about ½ hour after which the mixture is diluted with, for example, petroleum ether, benzene or toluene and the amine isolated. Alternatively, the imine is hydrolyzed with 0.5 to 1 N HCl solution, and the aqueous phase evaporated to afford the amine as the hydrochloride salt Compounds of formula I wherein Z is

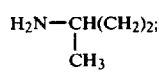

Y is $CH_2F$ or $CHF_2$; and $R_1$ is hydrogen are prepared by reducing a ketone of the formula

  (XII)

wherein Z' is

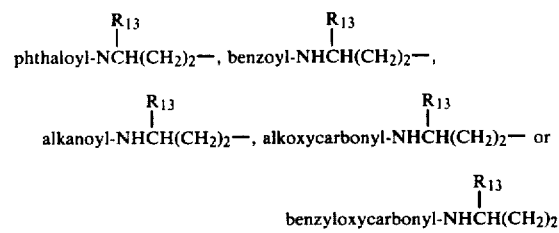

wherein the alkanoyl moiety has from 2 to 5 carbon atoms and is straight or branched, the alkoxy moiety has from 1 to 4 carbon atoms and is straight or branched, Y is $CH_2F$ and $CHF_2$ and $R_{13}$ is methyl. The ketones are reduced to the corresponding alcohol which is treated with one equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a suitable solvent. Suitable solvents include ethers such as diethyl ether, tetrahydrofuran or p-dioxane, benzene or dimethoxyethane. The reaction is conducted at about 0° to 100° C., preferably about 25° C., for a period of about one-half hour to 24 hours under an inert atmosphere such as nitrogen or argon. The thus obtained imido derivative is then hydrolyzed to the free amine.

The compounds of general formula (XII) wherein Y is $FCH_2$— are prepared by treating a compound of the formula

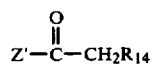  (XIII)

wherein Z' is defined as above and $R_{14}$ is a suitable leaving group, such as chlorine, bromine or iodine, mesylate, tosylate, triflate or trifluoroacetate with an appropriate fluorinating reagent, such as, potassium fluoride, silver fluoride, cesium fluoride, thallium fluoride, tetrabutylammonium fluoride in a suitable solvent. Suitable solvents include solvents such as dimethoxyethane, dimethylsulfoxide, dimethylformamide, ethylene glycol, acetonitrile, acetone, benzene or hydrogen fluoride. The reaction is conducted at a temperature of from about 0° to 200° C. for a period of about 2 to 48 hours. The leaving group $R_{14}$ may also be a diazo group in which case the fluorinating reagent employed is hydrogen fluoride/pyridine. Suitable solvents for the reaction wherein $R_{14}$ is a diazo group are aprotic solvents such as diethyl ether, tetrahydrofuran and pentane. The reaction time varies from about 30 minutes to 24 hours at a temperature ranging from about −20° to 65° C. Illustratively, a compound of the formula

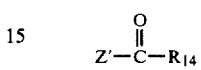

as defined above wherein $R_{14}$ is a diazo group in a suitable aprotic solvent is added to a solution of hydrogen fluoride/pyridine and cooled to −10° C. The reaction mixture is stirred vigorously at −10° C. for 1 hour, warmed to about 25° C. for 2 hours and then poured over ice. The organic phase is separated, washed with a base such as sodium bicarbonate, dried over magnesium sulfate and concentrated under vacuum to afford the appropriate fluoromethyl ketone derivative of formula (XII).

The diazo ketone derivatives, that is, the compounds of formula (XIII) wherein $R_{14}$ is a diazo group, can be obtained via the corresponding acid halide represented by a compound of the formula

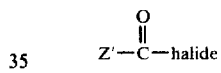

wherein halide may be, for example, chloride and Z' has the meaning defined in formula (XII). The acid halide contained in an aprotic solvent, as for example diethyl ether, tetrahydrofuran, pentane, hexane, benzene, dimethoxyethane or dioxane, is added to a solution of diazomethane in ether cooled to about −40° to 20° C., followed by vigorous stirring at about 25° C. for about 1 to 24 hours. The diazo ketone derivative so obtained can be isolated using standard procedures such as evaporation of the solvent with subsequent purification by recrystallization of chromatography. Alternatively, the reaction mixture can be treated with an appropriate fluorinating reagent as described above without isolation.

The appropriately substituted diazo ketone derivative described above can be used to prepare compounds of formula (XIII) wherein $R_{14}$ is, for example, halogen, mesylate, tosylate, triflate, or trifluoroacetate using procedures generally known to the art. To obtain compounds of general formlua (XIII) wherein $R_{14}$ is halogen, such as, chlorine, bromine, or iodine the corresponding compound of formula (XIII) in which $R_{14}$ is a diazo group is treated with either aqueous hydrogen chloride, hydrogen bromide or hydrogen iodide in a suitable aprotic solvent. In order to obtain compounds of formula (XIII) wherein $R_{14}$ is mesylate, tosylate, triflate or trifluoroacetate, the corresponding diazo ketone derivative, wherein $R_{14}$ is a diazo group is dissolved in a suitable aprotic solvent and treated with dilute sulfuric acid to yield the corresponding benzyl methanol ketone derivative. Lastly, the benzyl methanol ketone is esterified with an appropriate acid chloride or acid anhydride utilizing methane sulfonic acid, p-toluene sulfonic acid, trifluoromethyl sulfonic acid or trifluoroacetic acid.

The acid halides, that is, compounds of the formula

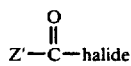

as described above, are known compounds which can be prepared from the corresponding acids. Thus, for example, treatment of the appropriate acid with thionyl chloride in an aprotic solvent, such as, diethyl ether, tetrahydrofuran, benzene or dichloromethane at a temperature ranging from about 0° C. to the reflux temperature of the solvent for about 1 to 24 hours results in the foundation of the corresponding acid halide. Alternatively, treatment of the appropriate acid with oxalyl chloride in one of the aprotic solvents described above at a temperature of about 0° to 40° C. for about 1 to 24 hours also results in the preparation of the corresponding acid halide.

The compounds of general formula (XII) wherein Y is $FCH_2$— and Z' is other than

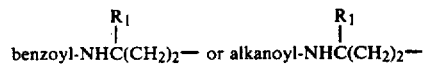

may also be obtained by treating a compound of the formula $$Z_2—R_{15} \qquad (XIV)$$

wherein $Z_2$ is

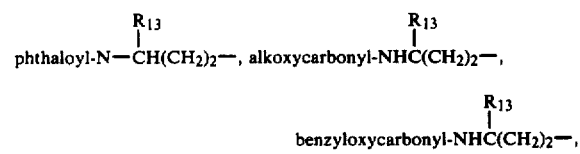

$\beta$-methylthioethyl or $\beta$-benzylthioethyl; $R_{13}$ is methyl; and $R_{15}$ is chlorine, bromine or iodine, mesylate or tosylate. Thus, a compound of formula (XIV) is reacted with triphenylphosphine or tri-(lower)-alkylphosphine, for example, tri-n-butyl-phosphine, in a solvent such as benzene, toluene, methanol, ethanol, acetonitrile, tetrahydrofuran, diethyl ether or dimethoxyethane. The reaction is conducted at a temperature ranging from 25° C. to the reflux temperature of the solvent for a period ranging from about 10 minutes to 48 hours. On cooling the precipitate which forms is washed with solvent and recrystallized to give the appropriate phosphonium salt. The triphenylphosphonium or trialkylphosphonium salt is added to an excess (up to 25%) of sodium or lithium metal dissolved in liquid ammonia to which a catalytic amount of ferric nitrate is added. Stirring is continued for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting substituted methylidenephosphorane is collected. The methylidenephosphorane is treated with a lower alkyl ester of monofluoroacetic acid in a solvent such as benzene, toluene, diethyl ether, tetrahydrofuran or dimethoxyethane. The reaction is conducted under an inert atmosphere such as nitrogen or argon at a temperature ranging from about 0° C. to the reflux temperature of the solvent for a period of from about 30 minutes to 24 hours. The reaction mixture is concentrated by distillation to yield an olefin. The olefin is treated with an aqueous mineral acid, such as hydrochloric or hydrobromic acid or an organic acid such as trifluoroacetic acid or p-toluene sulfonic acid in the presence of a co-solvent such as tetrahydrofuran, diethyl ether, or benzene for a period of from about 30 minutes to 24 hours at a temperature ranging from about 0° C. to the reflux temperature of the solvent. The amount of acid employed may vary from a catalytic amount to a concentrated acid solution.

As used in general formula (XIV)

the term phthaloyl-N—$\overset{R_{13}}{\underset{|}{C}}$H(CH$_2$)$_2$— is taken to mean the group

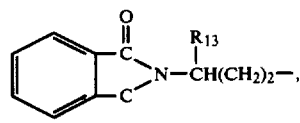

the term alkoxycarbonyl-NH$\overset{R_{13}}{\underset{|}{C}}$H(CH$_2$)$_2$— is taken to mean the group alkyl-O—$\overset{O}{\underset{\|}{C}}$—NH$\overset{R_{13}}{\underset{|}{C}}$H(CH$_2$)$_2$—, the term benzyloxycarbonyl-NH$\overset{R_{13}}{\underset{|}{C}}$H(CH$_2$)$_2$— is taken to mean

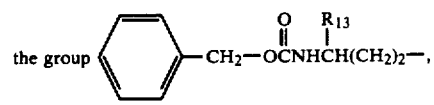

wherein $R_{13}$ has the meanings defined in formula (XIV) and alkyl is a straight or branched group having from 1 to 4 carbon atoms.

Compounds of general formula (XII) wherein Y is $F_2CH$—are obtained by treating [[(methylsulfinyl)methyl]thio]methane or [[(ethylsulfinyl)methyl]thio]ethane with a suitable strong base followed by alkylation with an appropriate derivative of the formula $$Z'—R_{16} \qquad (XV)$$

wherein in formula (XV) the symbol Z' has the meaning previously defined in formula (XII) and $R_{16}$ is chlorine, bromine, iodine, mesylate or tosylate. The thus formed Z' substituted sulfinyl derivative is treated with a suitable strong base followed by alkylation using an appropriate halomethylhalo alkylating reagent selected from chlorodifluoromethane, bromodifluoromethane, and difluoriodomethane. The alkylation reaction is followed by a hydrolysis using an aqueous acid solution.

Suitable strong bases which may be employed in preparing the difluoromethyl substituted ketone derivatives as described above are sodium hydride, dilithium acetylide, lithium diisopropylamide, butyllithium, potassium tert-butoxide, sodium tert-butoxide, lithium tert-butoxide, phenyllithium, methyllithium, sodium amide, lithium amide or potassium hydride.

The alkylation reaction described in preparing the difluoromethyl ketone derivatives are carried out in an appropriate solvent, for example, tetrahydrofuran, diethyl ether, hexamethylphosphortriamide, dimethylsulfoxide, or benzene. The reaction is conducted at a temperature ranging from about −78° to 65° C. for a period of from about 30 minutes to 24 hours. Preferably, a temperature of about 40° C. is utilized for the difluoromethyl alkylation step. The alkylated sulfinyl intermediates are isolated by quenching with a brine solution followed by extraction utilizing diethyl ether, dichloromethane, or benzene. The alkylated sulfinyl intermediates are recovered from the combined extracts.

Hydrolysis of the alkylated sulfinyl derivatives to the ketone is achieved using an aqueous mineral acid solution, such as, hydrochloric, hydrobromic, perchloric or sulfuric acids in a solvent such as tetrahydrofuran, acetonitrile, diethyl ether or benzene. The hydrolysis is conducted at a temperature ranging from about −20° to 105° C., preferably about 25° C. for a period of from about 30 minutes to 24 hours, preferably about 2 hours. Generally, a solution of 0.3 equivalents of mineral acid in 1.5% water is employed. The specific examples described below further illustrate the preparation of the difluoromethyl ketone derivatives of formula (XII).

The compounds of formulas (XIV) and (XV) wherein $R_{15}$ and $R_{16}$ are halogen are known to the art or can be prepared from an appropriate carboxylic acid derivative having the formula $$Z_4-COOH \qquad (XVI)$$

wherein $Z_4$ is

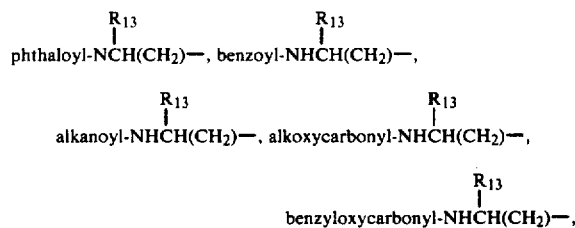

methylthiomethyl or benzylthiomethyl. These acids are known to the art or can be obtained by known procedures from the corresponding unprotected amino acids. The compounds of formulas (XIV) and (XV) wherein $R_{15}$ and $R_{16}$ are mesylate or tosylate may be prepared by treating the corresponding derivatives in which $R_{15}$ and $R_{16}$ are halogen with a metal salt of methanesulfonic acid or p-toluenesulfonic acid. Illustratively, the sodium salt of methanesulfonic acid or p-toluenesulfonic acid can be utilized.

Reduction of the ketones of formula (XII) to the corresponding alcohols is achieved chemically using 1 to 10 equivalents of a metal hydride, such as lithium borohydride, sodium borohydride, sodium cyanoborohydride, or lithium aluminum hydride. In addition the ketones can be reduced with borane or dimethylthioborane or catalytically reduced using, for example, Raney nickel, rhodium, palladium on charcoal, or platinum oxide. In general, the reaction time varies from about 10 minutes to 24 hours and the temperature at which the reduction is conducted can range from about −40° C. to 100° C. depending upon the particular reducing reagent employed. When hydride or borane reduction is employed the reaction is conducted in a suitable solvent for a period of time from about 10 minutes to 24 hours with temperatures ranging from about −40° C. to 65° C. Suitable solvents that can be employed for reduction of compounds of general formula (XII) include lower alcohols, such as methanol or ethanol, or ethers, such as diethyl ether or tetrahydrofuran. When catalytic reduction is employed the reaction time varies from about 1 hour to 24 hours, the reaction temperature ranges from about 25° to 100° C. and the hydrogen pressure can range from 1 to 120 atmospheres.

Hydrolysis to the amine and the removal of any distal amine protecting group is achieved using a strong mineral acid such as hydrochloric acid, hydrobromic acid or sulfuric acid, or an organic acid such as toluenesulfonic acid or trifluoroacetic acid. The hydrolysis is conducted in water or an aqueous solvent at the reflux temperature for a period of from about 4 to 48 hours. Alternatively, 1 to 3 equivalents of hydrazine, methylhydrazine or methylamine can be utilized at a temperature of from about 25° C. to the reflux temperature of the solution for about 1 to 12 hours, followed by treatment with a strong mineral acid or organic acid as described above.

Compounds of formula I wherein Z is

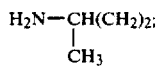

$R_1$ is hydroxy; and Y is C CH, or as hereinafter indicated the alkynyl group, are prepared by the hydrolysis of the alkylated compounds 5, described above. The desired alkylating reagents $R_8X$ that are employed can be prepared by methods known to the art. Thus, the reagent

can be prepared by reacting 3-bromo-n-propylamine hydrochloride with benzaldehyde and an organic trialkylamine, such as triethylamine, in a solvent such as diethyl ether, tetrahydrofuran, dioxane, chloroform or dichloromethane. The reactant

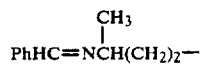

is prepared by reacting 3-aminobutylbromide hydrobromide with benzaldehyde and an organic amine such as treithylamine. The compound 3-aminobutylbromide hydrobromide is a known compound that can be prepared from the corresponding alkanol by treatment with concentrated HBr at a temperature of from 25° C. to 110° C. for a period of from 1 to 12 hours. The γ-aminoalkanol derivative is obtained by treating an appropriate β-keto-alkanoic acid ester the formula

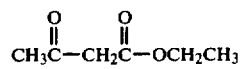

The β-keto-alkanoic acid ester is treated with hydroxylamine to form the corresponding oxime, which is reduced with lithium aluminum hydride in ether or tetrahydrofuran at a temperature of from 25° to 50° C. for a period ranging from 1 to 12 hours. Subsequent hydrolysis of the ester moiety results in the formation of the γ-aminoalkanol.

The alkylating reaction may be carried out in an aprotic solvent, for example, benzene, toluene, ether, tetrahydrofuran, dimethylsulfoxide or hexamethyl phosphortriamide. The reaction temperature varies from about −100° to 25° C. preferably about −70° C. and the reaction time varies from about ½ hour to 24 hours.

Removal of the protecting groups, as represented in the reaction scheme in the step going from compounds 5 to the desired amines, is ahcieved by treatment with aqueous acid, for exaple, hydrochloric acid followed by aqueous base, for example, sodium hydroxide or potassium or treatment with phenylhydrazine, hydroxylamine or hydrazine then with aqueous base.

The individual optical isomers of compounds of formula I wherein $R_1$ is carboxy or hydrogen are resolved using a (+) or (−) binaphthylphosphoric acid salt in accordance with the procedure of R. Viterbo et al., Tetrahedron Letters 48, 4617 (1971). Other resolving agents such as (+) camphor-10-sulfonic acid may also be employed. Alternatively, when Z is

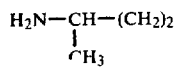

or $H_2N(CH_2)_n$, resolution is achieved via the lactam of said compounds. The thus resolved acids and amines may be employed in the same manner as described hereinabove for the racemic mixtures.

The compounds described herein are useful in inhibiting the growth of protozoa in animals. The term "animals" is intended to include inter alia mammals, such as mice, rats, guinea pigs, rabbits, ferrets, dogs, cats, cows, horses and primates including man. Also encompassed within the term animals are both fish and fowl. The term "fowl" is intended to include male or female birds of any kind including parrots and canaries, but is primarily intended to encompass poultry which are commercially raised for eggs or meat. Accordingly, the term "fowl" is particularly intended to encompass hens, cocks and drakes of chickens, turkeys and ducks.

The term "protozoa" is intended to include those members of the subphyla Sarcomastigophora and Sprozoa of the phylum Protozoa. More particularly, the term "protozoa" as used herein is intended to include those genera of parasitic protozoa which are important to man because they either cause disease in man or his domestic animals. These genera are for the most part found classified in the superclass of Mastigophora of the subphylum Sarcomastigophora and the class of Telosporea of the subphylum Sporozoa in the classification according to Baker (1969). Illustrative genera of these parasitic protozoa include Histomonas, Trypanosoma, Giardia, Trichomonas, Eimeria, Isopora, Toxoplasma and Plasmodium.

Excluded from the superclass of Mastigophora is the genus Leishmania, certain species of which cause the tropical desease of Leishmaniasis in man. Also, specifically excluded from the genus Trypanosoma, as used in this invention, are the species Trypanosoma cruzi, which can cause Chagas' disease in man, and the species Trypanosoma lewisi. The compounds described herein have been found not to be particularly effective against these species.

On the other hand, the compounds of Formula I are particularly useful in inhibiting the growth of Trypanosoma brucei, the causative agent for nagana, or the tsetse-fly disease of horses and cattle in central Africa. The compounds described herein are also remarkably effective in inhibiting the growth of Eimeria tenella, a species of protozoa causing coccidiosis in fowl.

Indeed, a preferred embodiment of the present invention is the use of these compounds to inhibit the growth of intestinal coccidia in commercial poultry. The economic importance of intestinal coccidia is highly significant. Thus in 1972, the estimated loss to the poultry industry in the United States due to coccidial infections was approximately 47 million dollars. Due to the rapid development of drug resistance by coccidia, and due to the relatively high toxicity of some of the drugs used in the treatment of coccidiosis, there is a need for effective coccidiostats that are non-toxic and to which intestinal coccidia do not develop rapid drug resistance.

It is not exactly understood how the compounds of this invention are able to inhibit the growth of protozoa. Inter alia, the compounds described herein are irreversible inhibitors of ornithine decarboxylase and S-adenoxylmethionine decarboxylase. As irreversible inhibitors of these enzymes, these compounds inhibit polyamine formation which may be required for protozoal cell division. In any event, the practice of this invention is not limited to any particular mode or theory of action whereby the compounds of this invention are able to effectively inhibit the growth of protozoa.

The effect of the compounds of general formula (I) upon the growth of protozoa, and more particularly upon the growth of coccidia, can be demonstrated using Eimeria tenella and two week old male white leghorn chicks as the test animals. The birds are kept in batteries and both the infected and non-infected birds are housed in separate rooms to assure the maintenance of coccidia-free birds. Each experimentally infected bird receives 100,000 sporylated oocysts via gavage. The test compound is administered in the particular dosage desired through the drinking water and drug-free mash is provided ad libitum. To evaluate the effect of the active ingredient on E. tenella infections, the chicks are sacrificed with carbon dioxide, necropsied, generally at day five of the study, and cecal lesions evaluated.

The inhibition of protozoal growth can also be determined using Trypanosoma brucei brucei, which is the causative agent of bovine trypanosomiasis (nagana) in Africa. The related species Trypanosoma brucei rhodesiense and Trypanosoma brucei gambiense are the causative agents for African sleeping sickness in humans.

In general, drug activity is tested against established infections of a pleomorphic EATRO 110 isolate of T. b. brucei in mice. Test animals are infected with $5 \times 10^5$ parasites twenty four hours prior to testing. Control animals so infected generally die 5 days subsequent to innoculation. The compound to be tested is administered to the test animals via their drinking water in varying dosages. Animals cured of the infection remain parasitefree more than 30 days after the deaths of the control animals as indicated by an examination of blood smears.

The compounds described herein are employed in amounts that are effective in inhibiting protozoal growth. These amounts will depend, or course, upon various factors, such as the type and nature of the protozoal infection, the activity of the specific compound, the age, sex and species of animal treated and whether the treatment is prophylactic or therapeutic. In general, the compounds described herein can be orally or parenterally administered at a dialy dose ranging from 5 mg/kg to 7 g/kg. Preferably, in the case of Trypanosoma infections the dosage range is from about 600 mg/kg to about 2 g/kg. In the case of Eimeria infections the dose can be lowered, ranging from about 15 mg/kg to about 1 g/kg.

Due to the low toxicity of the compounds described herein, the compounds can be safely administered ad libitum via the drinking water of the test animals in the treatment of coccidiosis in fowl. Generally speaking, concentrations of the active ingredient ranging from about 0.01% to about 2% are suitable, depending primarily upon the nature of the protozoal infection to be treated whether prophylactic or therapeutic, the severity of the infection and the period of treatment.

Thus, for example the compound 2-difluoromethyl-2,5-diaminopentanoic acid can be effectively administered to chickens for the treatment of coccidiosis one day prior to infection as a 2% solution. Alternatively, a prophylactic course of treatment can be utilized 8 days prior to infection utilizing concentrations of 2-difluoromethyl-2,5-diaminopentanoic acid as low as 0.015% in the drinking water of chickens. Preferably, a prophylactic concentration of from 0.06% to about 1.0% is preferred.

This prophylactic treatment for the inhibition of protozoal growth provides one of the principle advantages to the use of the decarboxylase inhibitors described herein. Thus, in the case of coccidia infections in chickens, for example, *Eimeria tenella* grows intracellularly in the epithelial cells of the caecum as a trophozoite stage. Subsequently, these cells undergo a form of multiple mitosis to form a large number of merozoites. These merozoites are released as the host cell lyses and serve to extensively infect fresh cells. The result is that the wall of the caecum is badly damaged, leading to severe blood and fluid loss and finally death. Moreover, during the life cycle of *E. tenella*, resistant oocysts are produced which are voided in the faeces of chickens. Chickens being coprophagous in nature, the disease is rapidly spread by contamination of their food supply. Accordingly, coccidial infections in commercial flocks, when they occur, are epidemically treated with massive doses of currently available chemotherapeutic agents, that are primarily cidal in nature. Consequently, medicated feeds are now routinely employed in commercial flocks, so that all commercial fowl now receive almost constant medication to prevent outbreaks of coccidiosis from occurring.

The fact that the decarboxylase inhibitors herein described can be prophylactically administered, enables the host to overcome either a subsequent natural or artificial induced infection enzymatically via an inhibitory mechanism rather than via a cidal action. Thus, in the case of an *E. tenella* infection, the infection is curtailed in a manner that enables the host to avail itself of its own body defense mechanisms. The resulting antibodies which are produced via such a controlled infection, serve to further permanently immunize the host from future *E. tenella* infections.

The pharmaceutical compositions that are particularly suited for the prophylaxis or treatment of protozoal infections in fowl comprise the heretofore described α-substitutedamines or the α-substituted-α-amino acids in combination with a pharmaceutically acceptable carrier. Advantageously, the antiprotozoal compositions are prepared by admixing the active compound with an inert carrier material. Typical carriers include talc, clay, pumice, silica, chalk, diatomaceous earth, walnut shell flour and equivalents thereof. Alternatively, the active ingredient can be admixed with a commercial feedstuff or vitamin and mineral pre-mix particularly adapted for fowl.

In most cases a concentrated aqueous solution of the active ingredient is employed in the management and treatment of coccidiosis in fowl. The compounds described, for the most part, are highly soluble, particularly in the form of their salts. Such solutions may advantageously contain preservatives, such as parabens, benzyl alcohol, phenol or thimerosal. In addition, isotonic agents, sugars, stabilizing or buffering agents can be usefully employed.

The compounds of formula (I) can be used in conjunction with other known drugs currently in use for the chemotherapy and chemoprophylaxis of disease caused by parasitic protozoa. Generally, this has the effect of decreasing the amount of enzyme inhibitors administered. Such drugs include, among others: Antrycide, quinapyramine; Berenil, Diminazene aceturate; Pentamidine isethionate; Primaquine; Tryparsamide; Amicarbalide; Amprolium; Amphotericin B; quinine; Monensin; Minocycline, 7-dimethylamino-6-demethyl-6-deoxytetracycline; Clindamycin, 7-deoxy-7(S)-chlorolincomycin; Buquinolate; Robenidine; and Nicarbazin. In some instances the compounds of formula (I) actually enhance or potentiate the effects of these drugs.

Of particular interest in this regard is the compound 2,5-diamino-2-difluoromethylpentanoic acid which has been shown to act synergistically with the antiprotozoal agents Antrycide, quinapyramine, Pentamidine isethionate and Amicarbalide. Thus, the 2,5-diamino-2-difluoromethylpentanoic acid concentration can be reduced by about four-fold when used in combination with subcurative doses (less than 1.0 mg/kg) of these drugs.

Additionally, the compounds of formula (I) can be used in combination with other known cytotoxic agents for the chemotherapy and chemoprophylaxis of parasitic diseases, particularly trypanosomiasis. Such cytotoxic agents include the antineoplastic antibiotic Bleomycin as well as other well-known cytotoxic agents, as for example, cyclophosphamide, methotrexate, prednisone, 6-mercaptopurine, procarbozine, daunorubicin, vincristine, vindesine, vinblastine, chlorambucil, cytosine arabinoside, 6-thioguanine, thio TEPA, 5-fluorouracil, 5-fluoro-2-deoxyuridine, 5-azacytidine, nitrogen mustard, 1,3-bis(2-chloroethyl)-1-nitrosourea (BCNU), 1-(2-chloroethyl)-3-cylohexyl-1-nitrosourea (CCNU), busulfan or adriamycin.

Of particular interest in the treatment of trypanosomiasis in general, and more particularly in the treatment of nagana in cattle, is the use of the enzyme inhibitor 2,5-diamino-2-difluoromethylpentanoic acid in combination with the antitumor antibiotic Bleomycin. This particular enzyme inhibitor appears to act synergistically with Bleomycin. Thus, mice infected with *Trypanosoma brucei* are cured after three days upon daily i.p. administration of Bleomycin at a dosage of 7 mg/kg. Similarly, trypanosome infections in mice are cured by the administration of a 1% solution of 2,5-diamino-2-difluoromethylpentanoic acid in the drinking water for 3 days.

The results of several combination experiments indicate that cures are consistently effected with 0.5 mg/kg of Bleomycin in combination with 0.5% of 2,5diamino-2-difluoromethylpentanoic acid administered via drinking water. Alternatively, cures are effected with concentrations of 0.25 mg/kg of Bleomycin in combination with only 0.25% of 2,5-diamino-2-difluoromethylpentanoic acid in the drinking water. A combination of 0.1 mg/kg of Bleomycin and 0.1% of 2,5-diamino-2-difluoromethylpentanoic acid has no effect. Thus, the curative dosage combinations reflect a reduction in Bleomycin drug dosage of from ½ to 1/28 of the curative dose of the drug used singly, when used in combination with a subcurative dose of from ½ to ¼ of the curative dose of 2,5-diamino-2-difluoromethylpentanoic acid.

The invention described and claimed herein is more particularly illustrated in conjunction with the following Examples specifically describing how the compounds of this invention can be prepared and utilized.

EXAMPLE 1

2-Difluoromethyl-2,5-diaminopentanoic acid

Under nitrogen a solution (500 ml) of 2 M butyllithium in hexane is added to a stirred solution of 143.1 ml of diisopropylamine in 1.5 liters of tetrahydrofuran at −78° C. after which 261 g (0.81 mole) of ornithine dibenzaldimine methyl ester in 1.5 liters of tetrahydrofuran is added. Upon completion of the addition the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1 N HCl (1.5 l) for 3 hours, the mixture extracted several times with chloroform and the aqueous solution evaporated to dryness. The oily residue is refluxed with 12 N hydrochloric acid (1.5 l ) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with 7-8 liters of acetone. The precipitated product is filtered off and washed with ethanol. The crude product is recrystallized by dissolving in about 150 ml hot water and treatment of the solution with hot ethanol (450 ml). On cooling crystals of 2-difluoromethyl-2,5-diaminopentanoic acid hydrochloride monohydrate separate 71 g (37%), m.p. 183° C.

EXAMPLE 2

α-Ethynyl-α,δ-diaminovaleric acid 11.8 g (0.048 M) of N-(3-trimethylsilylprop-2-ynyl)-benzenecarboximidate in 20 ml of tetrahydrofuran is added to lithium diisopropylamide, prepared from 4.9 g (6.78 ml, 0.048 M) of diisopropylamine in 60 ml of tetrahydrofuran and 23.6 ml of 2.05 M solution of n-butyllithium at −70° C. after which 9.5 g (0.042 M) of N-(3-bromopropyl)benzylimine is added, and the mixture is stirred at −70° C. for 5½ hours. To the reaction mixture is added 23.6 ml of a 2.05 M solution of n-butyllithium followed by the addition of 4.5 g (3.67 ml, 0.048 M) of methyl chloroformate. After 30 minutes at −78° C. the mixture is treated with brine, and the reaction product is isolated by ether extraction. The ether extract is evaporated and 300 ml of 3 N HCl is added to the resulting residue and the mixture is refluxed for 7 hours. On cooling the mixture is washed well with methylene chloride, made alkaline and washed again. The aqueous solution is acidified and concentrated to dryness. The residue is triturated with ethanol, filtered and the ethanol evaporated. The residue is dissolved in water, the pH adjusted to 6, and the solution is applied to a column of Amberlite 120 H+, eluting with 1 M NH₄OH which affords, upon recrystallization from ethanol-water, α-ethynyl-α,δ-diaminovaleric acid, M.P. 168–169 (dec.).

In the above procedure N-(3-bromopropyl)benzylimine is prepared from 3-bromopropylamine and benzaldehyde by procedures generally knon in the art.

EXAMPLE 3

1-Fluoromethyl-1,4-butanediamine dihydrochloride

To a solution of 40 mmole of diazomethane in 110 ml of ether cooled to 0° C. and magnetically stirred is added under nitrogen dropwise over a period of 1 hour a solution of 20 ml of 4-phthalimidobutyryl chloride in 75 ml of ether. Stirring is continued for 1 hour at 25° C. after which the reaction mixture is added to a solution of 40 ml of HF/pyridine precooled to 0° C. The resulting heterogeneous mixture is stirred at 25° C. for 1½ hours and then poured on ice water. The ether phase is separated, washed with a solution of bicarbonate, then with brine and dried over magnesium sulfate. Concentration of the solvent under reduced pressure affords a solid which is recrystallized from diethylether/pentane to give fluoromethyl 3-phthalimidopropyl ketone, m.p. 92° C.

To a solution of 550 mg (2.2 mmole) of fluoromethyl 3-phthalimidopropyl ketone in a mixture of 5 ml of tetrahydrofuran and 5 ml of methanol cooled to −20° C. is added a solution of 0.8 mmole of sodium borohydride in a mixture of 5 ml of tetrahydrofuran and 5 ml of methanol precooled to −20° C. The reaction mixture is stirred for 15 minutes at −20° C. and then neutralized with 2 M HCl to a pH of 1. The solvents are evaporated under reduced pressure and the residue is partitioned between water and chloroform. The organic phase is washed with brine, dried over magnesium sulfate and concentrated to give a residue which is recrystallized from tetrahydrofurandiethylether to afford 1-fluoro-5-phthalimido-2-pentanol, m.p. 85° C. A mixture of 264 mg (1.05 mmole) of 1-fluoro-5-phthalimido-2-pentanol, 170 mg (1.05 mmole) of the phthalimide, 302 mg (1.05 mmole) of triphenylphosphine and 201 mg (1.15 mmole) of diethylazodicarboxylate in 8 ml of tetrahydrofuran is stirred under nitrogen for 2 hours at 25° C. The solvent is evaporated under reduced pressure and the residue taken up in benzene. The insoluble material is discarded and the residue obtained after concentration of the filtrate is recrystallized from tetrahydrofuran-diethylether to give 1-fluoromethyl-1,4-butanediyl-bis-phthalimide, m.p. 112° C. A suspension of 3.1 g of 1-fluoromethyl-1,4-butanediyl-bis-phthalimide in 140 ml of concentrated HCl is heated at a reflux temperature for 3 days. The phthalic acid which precipitates on cooling to 4° C. is filtered off. The filrate is concentrated to about 20 ml and cooled to 4° C. The remaining phthalic acid which separates is filtered off and the filtrate is concentrated under reduced pressure. The residue is treated with 40 ml of boiling isopropyl alcohol 3 times and then recrystallized from absolute ethanol to give 1-fluoromethyl-1,4-butanediamine dihydrochloride, m.p. 154° C.

EXAMPLE 4

1-Fluoromethyl-4-methyl-1,4-butanediamine dihydrochloride

To a solution of 40 mmole of diazomethane in 110 ml of ether cooled to 0° C. and magnetically stirred is added under nitrogen dropwise over a period of 1 hour a solution of 20 ml of 4-phthalimido-4-methylbutyryl chloride in 75 ml of ether. Stirring is continued for 1 hour at 25° C. after which the reaction mixture is added to a solution of 40 ml of HF/pyridine precooled to 0° C. The resulting heterogeneous mixture is stirred at 25° C. for 1½ hours and then poured on ice water. The ether phase is separated, washed with a solution of bicarbonate, then with brine and dried over magnesium sulfate. Concentration of the solvent under reduced pressure affords a solid which is recrystallized from diethylether/pentane to give fluoromethyl 3-phthalimido-3-methylpropyl ketone.

To a solution of 550 mg (2.2 mmole) of fluoromethyl 3-phthalimido-3-methylpropyl ketone in a mixture of 5 ml of tetrahydrofuran and 5 ml of methanol cooled to −20° C. is added a solution of 0.8 mmole of sodium borohydride in a mixture of 5 ml of tetrahydrofuran and 5 ml of methanol precooled to −20° C. The reaction mixture is stirred for 15 minutes at −20° C. and then neutralized with 2 M HCl to a pH of 1. The solvents are evaporated under reduced pressure and the residue is partitioned between water and chloroform. The organic phase is washed with brine, dried over magnesium sulfate and concentrated to give a residue which is recrystallized from tetrahydrofuran-diethylether to afford 1-fluoro-5-phthalimido-5-methyl-2-pentanol. A mixture of 264 mg (1.05 mmole) of 1-fluoro-5-phthalimido-5-methylpentanol, 170 mg (1.05 mmole) of the phthalimide, 302 mg (1.05 mmole) of triphenylphosphine and 201 mg (1.15 mmole) of diethylazodicarboxylate in 8 ml of tetrahydrofuran is stirred under nitrogen for 2 hours at 25° C. the solvent is evaporated under reduced pressure and the residue taken up in benzene. The insoluble material is discarded and the residue obtained after concentration of the filtrate is recrystallized from tetrahydrofuran-diethylether to give 1-fluoromethyl-4-methyl-1,4-butanediyl-bis-phthalimide. A suspension of 3.1 g of 1-fluoromethyl-4-methyl-1,4-butanediyl-bis-phthalimide in 140 ml of concentrated HCl is heated at reflux temperature for 3 days. The phthalic acid which precipitates on cooling to 4° C. is filtered off. The filtrate is concentrated to about 20 ml and cooled to 4° C. The remaining phthalic acid which separates is filtered off and the filtrate is concentrated under reduced pressure. The residue is treated with 40 ml of boiling isopropyl alcohol 3 times and then recrystallized from absolute ethanol to give 1-fluoromethyl-4-methyl-1,4-butanediamine dihydrochloride.

EXAMPLE 5

1-Ethynyl-4-methyl-1,4-butanediamine

To 10.8 g (0.05 M) of 3-trimethylsilylprop-2-ynyl-1-iminobenzyl in 500 ml of tetrahydrofuran under nitrogen atmosphere at −78° C. is added n-butyllithium (0.05 M). After 10 minutes the dark red carbanion is treated with 11.3 g (0.05 M) of 4-bromo-2-iminobenzylbutane in 20 ml of tetrahydrofuran. After 3 hours at −78° C., fifty ml of water is added and the tetrahydrofuran is evaporated leaving a residue which is heated at reflux under nitrogen atmosphere with 100 ml of 6 N hydrochloric acid for 48 hours. Upon cooling the aqueous solution is washed with methylene chloride, made alkaline with aqueous sodium hydroxide and reextracted with methylene chloride. The methylene chloride extract is dried over magnesium sulfate, filtered, concentrated and distilled to afford 1-ethynyl-4-methyl-1,4-butanediamine.

EXAMPLE 6

Granules suitable for addition to the drinking water of poultry are prepared as follows:

|  | Grams |
|---|---|
| 2-Difluoromethyl-2,5-diaminopentanoic acid | 33.0 |
| Corn starch | 18.5 |
| Lactose | 48.2 |
| Zinc stearate | 0.3 |
|  | 100.0 |

The 2-difluoromethyl-2,5-diaminopentanoic acid is mixed with approximately 6 to 9 grams of lactose and passed through a fluid energy mill or micronizer to give a particle size of 1—25 microns. Water, 35 ml, is added to approximately 2.0 grams of the corn starch and blended to prepare a 5% starch paste. The micronized 2-difluoromethyl-2,5-diaminopentanoic acid—lactose powder, the remaining lactose and the remaining corn starch are well blended. The starch paste is added and blended, and the resulting mixture is passed through a No. 12 mesh screen. The resulting granules are dried at 38° C. to a moisture content of approximately 3%, ground through a U.S. Standard No. 12 screen and lubricated by mixing with 0.3 grams of zinc stearate.

EXAMPLE 7

A 10% stock solution for use in the treatment of coccidiosis is prepared by dissolving 37.5 grams of 2-difluoromethyl-2,5-diaminopentanoic acid in one gallon of water at room temperature. One part of this stock solution diluted with nine parts of water results in the preparation of a 1% medicated drinking water solution for poultry which is useful for the prevention of coccidiosis in poultry.

EXAMPLE 8

A medicated animal feed suitable for poultry is prepared utilizing the following ingredients. The birds are fed the medicated feed ad libitum.

|  | Percent by weight |  |
|---|---|---|
| Ground yellow corn | 60.3 |  |
| Soy bean oil meal | 33.0 |  |
| Alfalfa leaf meal | 1.0 |  |
| Dicalcium phosphate | 3.0 |  |
| Calcium carbonate | 1.0 |  |
| Iodized salt | 0.2 |  |
| 2-difluoromethyl-2,5-diaminopentanoic acid. | .33 |  |
| Vitamin-mineral-amino acid antibiotic mix to furnish the following per 100 pounds of feed: |  |  |
| Oxytetracycline | 0.5 | gm |
| Penicillin (as procaine salt) | 0.25 | gm |
| Manganese sulfate | 8 | gm |
| DL-methionine | 22.7 | gm |
| Riboflavin | 130 | mg |
| DL-calcium pantothenate | 930 | mg |
| Niacin | 1400 | mg |
| Pyridoxine | 130 | mg |
| Vitamin $B_{12}$ | 1 | mg |
| Choline chloride | 22.7 | gm |

| | Percent by weight |
|---|---|
| Vitamin A | 300,000 units |
| Vitamin D$_3$ | 25,000 units |

EXAMPLE 9

The following illustrates the effect of 2-difluoromethyl-2,5-diaminopentanoic acid on *Trypanosoma brucei brucei* infections in mice.

Groups of five mice weighing 20–25 g are innoculated with T.b. brucei (EATRO 110 isolate; 5×10$^6$ organisms/mouse). The compound is administered via drinking water, ad libitum, 24 hours following infection. Results are expressed as average survival (in days) beyond the death of the control animals, based upon an average survival of control animals of five days. Berenil (diminazene aceturate) is included as a control trypanocide. The results are indicated in Table I below.

TABLE I

| Drug | Treatment regimen | Total Dose (mg) | Average Survival (Days) |
|---|---|---|---|
| None | | 0 | 0 |
| 2-difluoromethyl-2,5-diaminopentanoic acid | | | |
| | 2% in drinking water, 6 days | 600$^a$ | >30$^b$ |
| | 2% in drinking water, 3 days | 300$^a$ | >30 |
| | 1% in drinking water, 6 days | 300$^a$ | >30 |
| | 1% in drinking water, 3 days | 150$^a$ | >30 |
| | 0.5% in drinking water, 3 days | 75$^a$ | 28.6 |
| | 0.1% in drinking water, 3 days | 15$^a$ | 2 |
| | 300 mg/kg p.o., daily 3 days | 22.5 | 26.3 |
| | 150 mg/kg p.o., daily 3 days | 11.3 | 22.8 |
| | 75 mg/kg p.o., daily 3 days | 5.6 | 19.2 |
| | 50 mg/kg p.o., daily 3 days | 3.8 | 0 |
| 2-methyl-2,5-diaminopentanoic acid | | | |
| | 2% in drinking water 3 days | 300$^a$ | 0 |
| diminazene aceturate | | | |
| | 2.5 mg/kg i.p. daily, 3 days | 0.2 | >30 |

$^a$Based upon a daily intake of 5 ml water/25 g mouse/day
$^b$Considered curative. Animals survived >1 month beyond controls; blood smears were negative for parasites after 1 month. Attempts at subinoculation of brain suspensions into uninfected animals remained negative after >30 days.

EXAMPLE 10

The following Example illustrates the effect of a 2% solution of 2-difluoromethyl-2,5-diaminopentanoic acid in the drinking water of chickens infected with oocysts of *Eimeria tenella*.

Twenty chickens are infected per os at day 1 with 100,000 oocysts of *E. tenella*. Ten of the animals are given drinking water containing a 2% solution of 2-difluoromethyl-2,5-diaminopentanoic acid. The remaining animals serve as controls. By day 3 all of the control animals demonstrate clinical signs of the disease. On day 7 all of the animals are sacrificed, cecal lesions are macroscopically examined and quantified as follows.

0 = No detectable macroscopic lesions.

+1 = Few scattered petachiae in the cecal wall; no thinkening of the wall and normal cecal contents present.

+2 = Lesions are numerous with noticeable loss in the cecal contents; cecal wall slightly thickened.

+3 = Large amounts of blood and tissue debris present, i.e., cecal cores; cecal wall greatly thickened, little if any normal cecal contents present.

+4 = Cecal wall greatly distended with much blood or cecal cores present. Cecal debris lacking or included in cores. (Dead bird also scores as +4.)

TABLE II

| | Lesion Scores In Individual Animals | Average Lesion Score For Group |
|---|---|---|
| Controls (N = 10) | +4 +3 +4 +4 +4 +4 +2 +4 +4 +4 | 3.6 |
| 2-difluoromethyl-2,5-diaminopentanoic acid treated | | |
| (N = 10) | +1 +1 +0 +1 +1 +3 +4 +4 +1 +1 | 1.7 |

EXAMPLE 11

Following essentially the same procedure as in the preceding Example, six chickens are administered a 2% solution of 2-difluoromethyl-2,5-diaminopentanoic acid (DFMO) in their drinking water for a period of 3 days. At day 1 this group of six chickens, in addition to two groups of ten chickens each, are all infected per os with 100,000 oocysts of *E. tenella* per chicken. One group of ten chickens serves as the control group, the other group of ten chickens receives a standard dose of Amprolium in their drinking water for the next 5 days. At present Amprolium is the coccidiostat of choice. On day 5 all of the animals are sacrificed and examined for evidence of disease using the lesion scoring index described in the preceeding Example. The following results are obtained.

TABLE III

| Treatment | No. Chickens | Days of Treatment | Mean Lesion Score |
|---|---|---|---|
| Control | 10 | — | 3.70 |
| 2% solution of DFMO | 6 | 3 | 0 |
| 0.120% solution of Amprolium | 10 | 5 | 0.3 |

EXAMPLE 12

The following Example illustrates the effect of varying doses of 2-difluoromethyl-2,5-diaminopentanoic acid on *Eimeria tenella* infections in chickens.

Following essentially the same procedure as in Example 10, the dosage of 2-difluoromethyl-2,5-diaminopropionic acid (DFMO) is varied as shown in Table IV below. Treatment with DFMO is started at day −1. The chickens are infected per os at day 0, and treatment is continued for an additional 5 days or a total of 6 days. The birds are sacrificed at day 5 and examined for evidence of disease using the lesion scoring index described in Example 10.

TABLE IV

| Treatment | No. Chickens | Days of Treatment | Mean Lesion Score |
|---|---|---|---|
| Control | 7 | — | 3.29 |
| 2% DFMO | 6 | 6 | 0 |
| 1.0% DFMO | 6 | 6 | 0.5 |
| 0.5% DFMO | 6 | 6 | 1.00 |

EXAMPLE 13

The following Example illustrates the effectiveness of a low prophylactic dose upon *Eimeria tenella* lesions in chickens.

Following essentially the same precedure set forth in Example 10, but varying the dose of 2-difluoromethyl-2,5-diaminopentanoic acid (DFMO) administered and the period of administration, the following results are obtained.

TABLE V

| Treatment | No. Chickens | Days of Treatment | Mean Lesion Score |
|---|---|---|---|
| Control | 9 | — | 3.33 |
| 2% DFMO | 9 | −1 thru +5 | 0 |
| 1% DFMO | 9 | −1 thru +5 | 0 |
| 0.5% DFMO | 9 | −1 thru +5 | 0 |
| 0.25% DFMO | 9 | −8 thru +5 | 0.44 |
| 0.125% DFMO | 9 | −8 thru +5 | 0 |
| 0.0625% DFMO | 9 | −8 thru +5 | 0.66 |

EXAMPLE 14

The following Example illustrates the acquisition of a permanent immunity towards *Eimeria tenella* infections in chickens.

Birds that have previously been treated wtih 2-difluoromethyl-2,5-diaminopentanoic acid at concentrations as low as 0.5% on days −8 through +5 relative to infection are challenged one week following completion of therapy as indicated in Table VI below. These results indicate that prophylactic therapy at low doses permits an adequate development of parasites in the absence of a disease state, thereby enabling the development of an immunity to subsequent *E. tenella* infections.

TABLE VI

| Treatment | No. of Chickens | Days of Treatment | Mean Lesion Score-Initial | Mean Lesion Score-Final |
|---|---|---|---|---|
| Control | 9 | — | 0 | 2.50 |
| 1.0% DFMO | 9 | −8 thru +5 | 0.33 | 0 |
| 0.5% DFMO | 9 | −8 thru +5 | 0 | 0 |

We claim:

1. A method of inhibiting the growth of protozoa in animals which comprises administering a protozoal inhibiting amount of an α-substituted amino acid or an α-substituted amine having the formula

wherein
R$_1$ is hydrogen or carboxy;
Y is selected from the group consisting of CH$_2$F, CHF$_2$, CF$_3$ and C≡CH;
Z is selected from the group consisting of H$_2$N—(CH$_2$)$_3$,

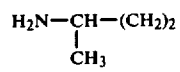

and H$_2$N-CH$_2$CH=CH; with the proviso that when R$_1$ is hydrogen, Y cannot be CF$_3$ and Z must be

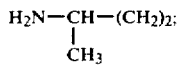

and the salts and individual optical isomers thereof.

2. A method according to claim 1 wherein R$_1$ is hydrogen.
3. A method according to claim 1 wherein R$_1$ is carboxy.
4. A method according to claim 1 wherein Z is

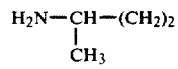

or H$_2$N—(CH$_2$)$_3$.

5. A method according to claim 1 wherein Y is CHF$_2$.
6. A method according to claim 1 wherein the animals are fowl and the α-substituted amino acid or α-substituted amine is administered to their drinking water at a concentration of from 0.01% to 2.0%.
7. The method according to claim 6 wherein the α-substituted amino acid or α-substituted amine is administered at a concentration of from 0.06% to 1.0%.
8. A method of inhibiting the growth of protozoa in animals which comprises administering a protozoal inhibiting amount of an α-substituted amino acid or an α-substituted amine having the formula

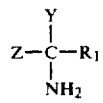

wherein
R$_1$ is hydrogen or carboxy;
Y is selected from the group consisting of CH$_2$F, CHF$_2$, CF$_3$ and C≡CH;
is selected from the group consisting of H$_2$N—(CH$_2$)$_3$,

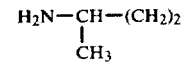

and H$_2$N-CH$_2$CH=CH; with the proviso that when R$_1$ is hydrogen, Y cannot be CF$_3$ and Z must be

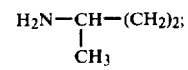

and the salts and individual optical isomers thereof in combination with an antiprotozoal agent selected from the group consisting of Antrycide, Pentamidine, Amicarbalide and Bleomycin.

9. A method according to claim 8 wherein R$_1$ is hydrogen.
10. A method according to claim 8 wherein R$_1$ is carboxy.
11. A method according to claim 8 wherein Z is

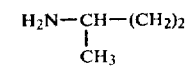

or $H_2N-(CH_2)_3$.

12. A method according to claim 8 wherein Y is $CHF_2$.

13. A method according to claim 8 wherein the animals are fowl and the α-substituted amino acid or α-substituted amine is administered to their drinking water at a concentration of from 0.01% to 2.0%.

14. A method according to claim 13 wherein the α-substituted amino acid or α-substituted amine is administered at a concentration of from 0.06% to 1.0%.

15. A method according to claim 1 wherein Y is $CH_2F$.

16. A method according to claim 8 wherein Y is $CH_2F$.

* * * * *